United States Patent [19]

Kim et al.

[11] Patent Number: 5,696,244
[45] Date of Patent: Dec. 9, 1997

[54] METHOD FOR PREPARING 1-N-ETHYLSISOMICIN

[75] Inventors: Joong-Hyup Kim; Sung Hoon Kim; Ghil Soo Nam; Ha Young Kim; Hyen Joo Son, all of Seoul, Rep. of Korea

[73] Assignee: Korea Institute of Science and Technology, Seoul, Rep. of Korea

[21] Appl. No.: 559,671

[22] Filed: Nov. 20, 1995

[30] Foreign Application Priority Data

Feb. 9, 1995 [KR] Rep. of Korea ............... 2382/1995

[51] Int. Cl.[6] .................................................. C07H 1/00
[52] U.S. Cl. .................... 536/13.9; 536/13.6; 536/13.7; 536/18.5
[58] Field of Search ............................... 536/13.9, 13.6, 536/13.7, 18.5

[56] References Cited

U.S. PATENT DOCUMENTS

| 4,002,742 | 1/1977 | Wright et al. | 536/13.6 |
| 4,029,882 | 6/1977 | Wright | 536/13.6 |
| 4,230,847 | 10/1980 | Nagabhushan et al. | 536/13.6 |
| 4,297,485 | 10/1981 | Umezawa et al. | 536/13.6 |
| 4,831,123 | 5/1989 | Tann et al. | 536/13.9 |

FOREIGN PATENT DOCUMENTS

| 529633 | 10/1985 | Spain . |
| 539016 | 11/1985 | Spain . |
| 87/02365 | 5/1987 | WIPO . |

OTHER PUBLICATIONS

Gribble et al., "Reactions of Sodium Borohydride in Acidic Media. I. Reduction of Indoles and Alkylation of Aromatic Amines with Carboxylic Acids," *J. Am. Chem. Soc.*, 96:7812–7814 (1974).

Marchini et al., "Sodium Borohydride–Carboxylic Acid Systems Useful Reagents for the Alkylation of Amines," *J. Org. Chem.*, 40:3453–3456 (1975).

Wright, "Synthesis of 1-N-Ethylsisomicin: A Broad-spectrum Semisynthetic Aminoglycoside Antibiotic," *J.C.S. Chem. Comm.*, 206–208 (1976).

Tattanahalli et al., "The Synthesis of Netilmicin via Complexing of Vicinal and non–Vicinal Amino–Hydroxyl Group Pairs with Divalent transition–Metal Cations," *Carbohydrate Research*, 130:243–249 (1984).

*Primary Examiner*—Elli Peselev
*Attorney, Agent, or Firm*—Townsend and Townsend and Crew

[57] ABSTRACT

1-N-ethylsisomicin represented by the following structural formula I and pharmaceutically acceptable salts thereof are useful antibacterial agents and can be prepared in high yields by a characteristic method comprising the steps of: chelating sisomicin with a chelating agent in a protic solvent; protecting the 3-,2'-and 6'-amino groups of the chelated sisomicin derivative with an acylating reagent; removing the chelating metal from the sisomicin derivative by use of ammonia water, to obtain a 3, 2', 6-N-trisubstituted sisomicin derivative; reacting the trisubstituted sisomicin derivative with an ethylating reagent in an aprotic organic solvent, to selectively ethylate the 1-amino group of the trisubstituted sisomicin derivative; and deprotecting the ethylated sisomicin derivative:

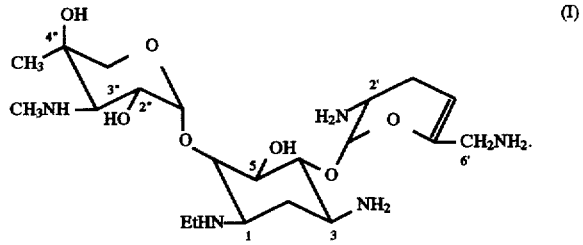

4 Claims, No Drawings

METHOD FOR PREPARING 1-N-ETHYLSISOMICIN

BACKGROUND OF THE INVENTION

1. Field of the invention

The present invention relates, in general, to a method for preparing 1-N-ethylsisomicin and, more particularly, to the use of a novel ethylating reagent in an appropriate solvent in ethylating only the 1-amino group of an acylated sisomicin derivative which results from conversion of selectively chelated sisomicin, leading to high yield of 1-N-ethylsisomicin with little or no by-products, especially, 1,1-N-diethylsisomicin.

2. Description of the Prior Art

1-N-Ethylsisomicin, represented by the following structural formula I,

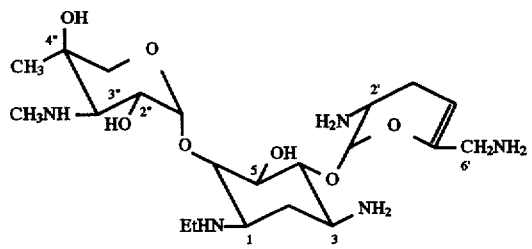

is a well known aminoglycoside antibiotic superior in treating bacterial infections in human bodies.

As shown in the structural formula I, 1-N-ethylsisomicin, derived from sisomicin, the precursor, consists of three hexose rings to which five amino groups are directly or indirectly attached. Although sisomicin itself is useful as an antibiotic, it is ethylated at the N atoms of the amino groups in order to prevent the deactivation by resistant bacteria, that is, to improve the antibiotic effect.

The ethylation of the amino group on the C-1 carbon atom of the sisomicin molecule but not on the other carbon atoms is typically achieved by initially protecting, all or a part of the amino groups on the C-3, C-2', C-6' and C-3" carbon atoms with a protecting group and ethylating the non-protected amino group on the C-1 carbon atom with a suitable reagent.

In this mono-ethylation technique, the step of protecting the amino groups except the one on the C-1 carbon atom is satisfactorily carried out but the step of ethylating only the amino group on the C-1 carbon atom is low in yield. In addition, the reaction conditions for this mono-ethylation is very sensitive to the object product such that its procedure is difficult to duplicate.

A wide variety of methods have been suggested to prepare 1-N-ethytsisomicin.

It is written in JCS Chem. Comm., 206 (1976) and U.S. Pat. No. 4,002,742 that 1-N-ethylsisomicin is prepared by reacting sisomicin sulfate with acetaldehyde in an aqueous solution. A significant disadvantage of this method is that the overall yield is very low, only 10–25%, which is directly attributed to the fact that the five amino groups led to an unusually high percentage of undesired by-products.

Suggested in U.S. Pat. No. 4,230,847 and Carbohydrate Research 130,243 (1984) are the processes marked in a substantial improvement in overall yield, 49%. Selective blocking of the 1- and 3"-amino groups, each neighboring a sterically available hydroxy group, is accomplished by forming transition metal salt complexes with transition metal salt such as $Co(OAc)_2$, $Cu(OAc)_2$, $Ni(OAc)_2$ etc., taking advantage of the chelating property of such transition metals. Also, the other amino groups, 3-, 2'- and 6'-amino groups, are protected by using anhydrous acetic acid. Thereafter, the transition metal cations are removed from the selectively N-protected complexes in a hydrogen sulfide atmosphere so as to obtain 3,2',6'-N protected sisomicin. After ethylation of the 1-amino group of this intermediate is carried out in water by means of acetaldehyde in the presence of a reducing agent, the protecting groups are taken off, to obtain the object compound.

Korean Pat. Laid-Open Publication No. 87-700632 and U.S. Pat. No. 4,831,123 disclose processes for converting selectively blocked sisomicin to a 1-N-imine derivative, then reducing the imine to a 1-N-ethylsisomicin under conditions which result in high yields of the desired compound with very low yields of interfering co-products. They consist broadly of reacting acetaldehyde with a selectively blocked sisomicin in an inert aprotic solvent, especially, dimethoxyethane, under anhydrous conditions, to form the corresponding 1-N-ethylidene derivative, reducing any excess of unreacted acetaldehyde present in the reactive mixture by utilizing a metal hydroxide as a reducing agent, reducing the 1-N-ethylidene group to the ethylamino group and removing all protecting groups. According to these processes, by-products can be considerably inhibited by improving the solubility of the intermediate 1-N-ethylidene derivative in the reaction solvent through introduction of silyl group into the hydroxyl groups of sisomicin, resulting in an increase in the overall yield.

Spanish Patent No. 529,633 suggests that, after the amino groups are protected by dihydropyran, the ethylation is accomplished by use of sodium hydroxide and ethyl iodide.

Spanish Patent No. 539,016 suggests that sisomicin is reacted with para-acetaldehyde and sodium cyanotrihydro borate in an aqueous sulfuric acid solution, to prepare 1-N-ethylsisomicin.

Of the suggested methods, ones disclosed in JCS Chem. Comm., 206 (1976) and U.S. Pat. No. 4,002,742 and the Spanish patents supra are considered as to be difficult to practice because of poor yield. In the case of the other methods, since the yield of the object compound sensitively fluctuates according the reaction conditions, such as solution type, pH change and so on, at the reduction step of 1-N-ethylidene group into 1-N-ethyl group, it is quite difficult to set the best conditions. Under the conditions used in these methods, unreacted or excess acetaldehyde seems to react with the already formed 1-N-ethylated sisomicin to form a considerable quantity of 1,1-N-diethylsisomicin, an undesired product, which leads to difficulty in the purification of the object compound and reduces the overall yield. Further, a large quantity of transition metal is required for the chelation of protecting groups. Furthermore, dimethyl sulfoxide or dimethyl formamide, are solvents with high boiling points, and should be handled in an anhydrous condition with care.

Particularly, the experiments that have been fulfilled by the present inventors reveal that acetaldehyde, the protecting group useful in the conventional techniques, is so volatile that it is very difficult to precisely control its amount, and the object compound, which is mono-ethylated at the amino group on the C-1 carbon atom, is further ethylated by acetahyde hyde-metal hydride reducing agent, so as to produce a large quantity of a compound into which two ethyl groups are introduced at the amino group on the C-1 carbon atom, a by-product.

SUMMARY OF THE INVENTION

While recognizing that there exists a need for a novel process for preparing 1-N-ethylsisomicin which avoids the aforementioned problems associated with the prior art, the present inventors applied the teaching described in JACS, 96, 7812 (1974) to Gordon W. Gribble and JOC, 40(23), 3453 (1975) to Felice Liberatore, wherein a composite of acetic acid and sodium borohydride is used as an alkylating reagent for amino groups and found that one molecule of ethyl group is introduced only on the 1-amino group of sisomicin with high yields by using acetic acid-sodium borohydride, acetic acid-triacetoxy sodium borohydride or acetic acid-potassium borohydride.

Based on intensive and thorough studies and research by the present inventors, it has been found that 1-N-ethylsisomicin having high yield can be prepared with high yields.

Accordingly, it is a principal object of the present invention to provide a method for preparing 1-N-ethylsisomicin in high yields of the object compound with low yields of interfering co-products.

In accordance with the present invention, the above object could be accomplished by providing a method for preparing 1-N-ethylsisomicin, comprising the steps of: chelating sisomicin with a chelating agent in a protic solvent; protecting the 3-, 2'-and 6'-amino groups of the chelated sisomicin derivative with an acylating reagent; removing the chelating metal from the sisomicin derivative by use of ammonia water, to obtain a 3, 2',6-N-trisubstituted sisomicin derivative; reacting the trisubstituted sisomicin derivative with an ethylating reagent in an aprotic organic solvent, to selectively ethylate the 1-amino group of the trisubstituted sisomicin derivative; and deprotecting the ethylated sisomicin derivative, and pharmaceutically acceptable salts thereof.

The present invention employs an ethylating reaction that has never been adopted in prior art techniques for the synthesis of 1-N-ethylsisomicin. Differing from some conventional techniques, the present invention has intermediates free of ethylidene group after the ethylating step. Thus, the present invention has significant advantages over the conventional art, including less reacting steps and higher yield. For example, instead of acetaldehyde, a mixture of acetic acid and sodium or potassium borohydride, or acetic acid and mono, di or triacetoxy sodium or potassium borohydride is employed as an ethylating agent in the method of the present invention. This ethylating reagent is able to produce only monoethylated object compound with little or no 1,1-N-diethylated co-product, a considerable amount of which is generated in the conventional methods, owing to excess acetaldehyde, a typical blocking group used in the conventional ethylating step.

In addition, the reactions utilizing this reagent are superior to those of the prior art techniques in that they are simple in their operation and convenient in purification their products.

Further, the chelating reaction as a preceding step for the purpose of protecting the 2-, 3'- and 6'-amino groups of sisomicin with an acyl group is effected by using zinc acetate $(Zn(OAc)_2)$, a transition metal salt which is handled with ease and has never been used in the prior art techniques, in an organic solvent that has a low boiling point.

DETAILED DESCRIPTION OF THE INVENTION

In accordance with the present invention, 1-N-ethylsisomicin (netilmicin) is prepared under the reaction procedure in that the mono-ethylation of sisomicin is effected by first reacting the starting material with amino-blocking compounds at the 3, 2' and 6' positions, to form a 3, 2',6'-N-blocked sisomicin derivative, followed by the introduction of an ethyl group on the 1-amino group and, finally, deprotecting all the blocking groups from the 1-ethylated intermediate.

In order to better understand the invention, this preparation procedure of 1-N-ethylsisomicin is summarized in the following scheme:

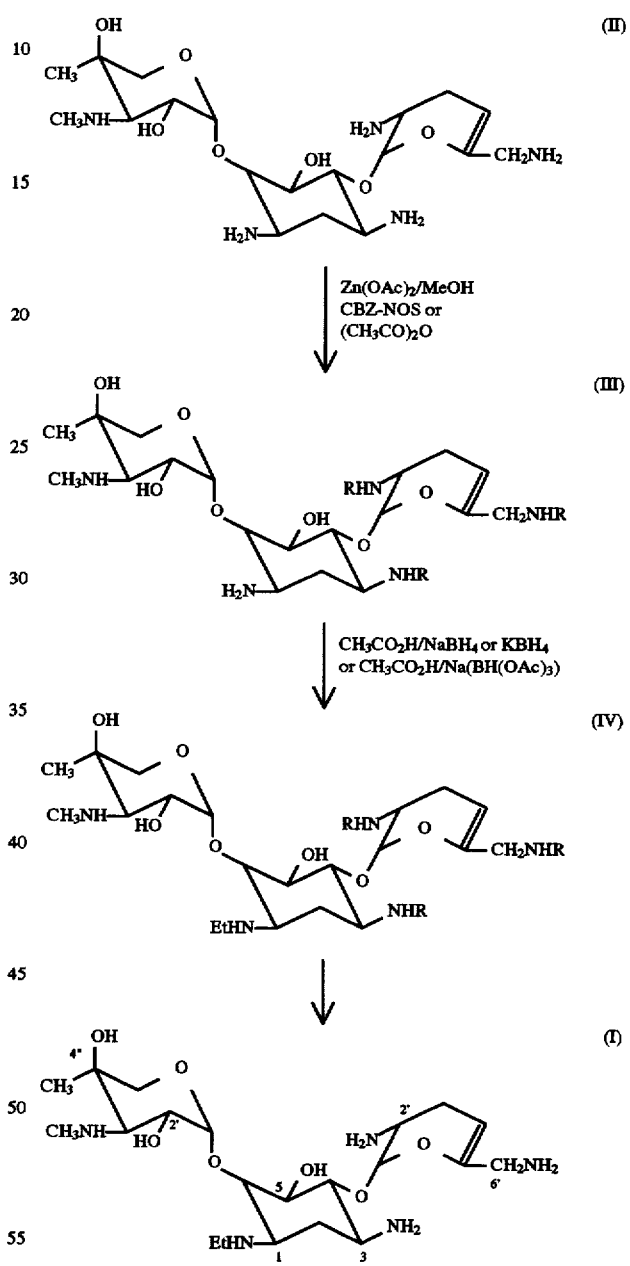

wherein R is protecting group such as benzyloxycarbony, acetyl and the mixtures thereof.

The preparation of compounds of Formula III from sisomicin, that is, selective protecting of the 3-, 2'- and 6'-amino groups of sisomicin, may be effected by well known methods such as those described in U.S. Pat. No. 4,230,847 and Carbohydrate Research 130, 243 (1984). In the present invention, however, zinc acetate (Zn(OAc) $_2.2H_2O$) as a transition metal salt is used with a lower alcohol solvent, such as methanol, ethanol, propanol, isopropanol or any mixture thereof, preferably methanol, to form zinc salt complexes on the 1- and 3"-amino groups of sisomicin, each neighboring a sterically available hydroxy group. Thereafter, an acylating reaction is executed on the non-blocked amino groups, so as to obtain 3, 2', 6'-tri-N-acylated sisomicin derivatives. The chromatographing of the acylated sisomicin derivatives with an eluting solution of ammonia water instead of hydrogen sulfide results in easily isolating 3, 2', 6'-tri-N-substituted sisomicin free of the transition metals.

Acylating reagents useful in the present invention are those that can produce an acyl group to protect the 3,2',6'-amino groups. Preferred acylating reagents include N-benzyloxycarbonyloxy, succinimide or anhydrous acetic acid.

Reaction of the obtained compounds of Formula III with an ethylating reagent in an aprotic organic solution results in high yield of the object compound of Formula IV without yielding 1,1-N-diethylsisomicin, a troublesome by-product.

Ethylating reagents useful in the present invention include a mixture of acetic acid with monoacetoxy, diacetoxy or triacetoxy sodium borohydride or potassium borohydride and a mixture of acetic acid with sodium borohydride or potassium borohydride. Preferred among the ethylating reagents is a mixture of acetic acid with triacetoxy sodium borohydride.

Concrete examples of the aprotic solvent useful in the present invention include halogenated alkyl solvents such as chloroform, methylene chloride and carbon tetrachloride; ethers such as tetrahydrofuran, dimethoxyethane and 1,4-dioxane; aromatic solvents such as benzene and toluene; nitriles such as acetonitrile, propionitrile and bonzonitrile and the mixtures thereof. Preferred among the aprotic solvents are chloroform, tetrahydrofuran or benzene.

Triacetoxy sodium borohydride may be synthesized according to the method disclosed in Chem. Comm., 535 (1975). For example, it may be stoichiometrically obtained by reacting 1 mole of acetic acid with 3 moles of sodium borohydride at a temperature of 25°±5° C. for 3 hours in one of the above-illustrated aprotic solvents, followed by solidification with ethyl ether and, finally, by drying the resultant solid.

Triacetoxy sodium borohydride is reacted with 3,2',6'-N-trisubstituted sisomicin (III) at a temperature of 20° to 50° C. for 1 to 4 days in the presence of acetic acid, to obtain a stoichiometry of 1-N-ethyl-3,2',6'-N-trisubstituted sisomicin (IV).

Alternatively, the 1-N-ethyl-3,2',6'-N-trisubstituted derivative of Formula IV can be obtained stoichiometrically in one-step wherein 3,2',6'-trisubstituted sisomicin (III) is added to the reaction system after excess acetic acid is reacted with one equivalent of sodium or potassium borohydride in one of the above-illustrated aprotic solvents at 0°–25° C. for 3 hrs.

Deprotection of the compounds of Formula IV can be effected by known techniques such as hydrolyzing in the presence of a base.

Then, the resulting deprotected sisomicin derivatives are isolated and purified by means of silica gel column chromatography. Accordingly, high yields of the compound of Formula I or the salts thereof, pharmaceutically useful compounds, are accomplished, in accordance with the present invention.

A better understanding of the present invention may be obtained in light of following examples which are set forth to illustrate, and are not to be construed to limit, the present invention.

EXAMPLE I

Preparation of 3,2',6'-tri-N-acetylsisomicin (III-a)

4.47 g of sisomicin (0.010 mol) was dissolved in 50 ml of methanol and then, added with 4.47 g of zinc acetate dihydrate (0.025 mol). Thereafter, this solution was stirred at room temperature for 15 hours. 3.31 ml of anhydrous acetic acid (0.035 mol) and 6.96 ml of triethyl amine in 15 ml of tetrahydrofuran was added dropwise to the stirred solution at room temperature for 4 hrs., and followed by additional stirring for 1 hr. The reaction mixture was distilled in vacuo, and the resultant residue was dissolved in a mixture solvent of conc. ammonia water (10 ml) and ethanol (20 ml). Thereafter, the organic layer was extracted three times with chloroform (40 ml) and then washed with brine (10 ml). The obtained organic layer was concentrated in vacuo, again. The resultant residue was subjected to silica gel column chromatography (70–230 mesh, 150 g) by use of an eluting solution comprising chloroform, methanol and 14% ammonia water in a ratio of 2:1:1. Concentration of the eluates thus obtained gave 5.32 g of the object compound (9.200 mmol), an ivory solid: 92% yield.

NMR (D$_2$O), 300 MHz): δ 1.22(s, 3H, C-CH$_3$), 1.95, 1.99, 2.07(9H, 3N-COCH$_3$), 2.78(s, 3H, N-CH$_3$), 3.22(d, 1H, J=9.5 Hz, H-3"), 5.17(d, 1H, J=4.2 Hz, H-1').

EXAMPLE II

Preparation of 3,2',6'-tri-N-Benzyloxycarbonylsisomicin (III-b)

4.47 g of sisomicin (0.01 0 mol) was dissolved in 50 ml of methanol and then, added with 4.39 g of zinc acetate dihydrate (0.020 mol). Thereafter, this solution was stirred at room temperature for 15 hrs. 10.20 g of N-benzyloxycarbonyloxy succinimide (0.04 mol) and 8.31 ml of triethyl amine in 80 ml of tetrahydrofuran was added dropwise to the stirred solution at room temperature for 6 hrs., and followed by stirring for 1 hr. The reaction mixture was distilled in vacuo, and the resultant residue was dissolved in a mixture solvent of conc. ammonia water (20 ml) and ethanol (30 ml). Thereafter, the organic layer was extracted three times with chloroform (80 ml) and then washed with brine (40 ml). The obtained organic layer was concentrated in vacuo, again. The resultant residue was subjected to silica gel column chromatography (70–230 mesh, 130 g) by use of an eluting solution comprising chloroform, methanol and 14% ammonia water in a ratio of 2:1:1. Concentration of the eluates thus obtained gave 6.74 g of the object compound (7.700 mmol), an ivory solid: 77% yield.

NMR (CDCl$_3$, 300 MHz): δ 1.11(s, 3H, C-CH$_3$), 2.58(s, 3H, N-CH$_3$), 4.89(s, 1H, H-4'), 5.00(s, 1H, H-1"), 5.02–5.10 (m, 6H, CH$_2$-Ph), 5.35(s, 1H, H-1'), 718–7.48(m, 15H, Ph)

Analysis calculated for: C$_{43}$H$_{55}$N$_5$O$_{13}$·1.5H$_2$O

Calculated: C, 60.07; H, 6.52; N, 8.24

Found: C, 60.40; H, 6.47; N, 8.10

EXAMPLE III

Preparation of 1-N-Ethyl-3,2',6'-tri-N-acetylsisomicin (IV-a)

A. Process A 15 g of triacetoxy sodium borohydride (0.07 mol) was added to 5.73 g of 3,2',6'-tri-N-acetylsisomicin (III-a) (0.01 mol) and 4.5 ml of glacial acetic acid (0.08 mol) in 50 ml of chloroform, and followed by stirring at 0°–50° C. for 20 hrs. After being cooled to room temperature, the reaction mixture was neutralized with 40 ml of a saturated sodium hydroxide solution, extracted three times with 50 ml of chloroform, and concentrated in vacuo. The resultant residue was subjected to column chromatography on silica gel by use of an eluting solution comprising chloroform, methanol and 14% ammonia water in a ratio of 30:10: 1. Freeze drying of the eluates thus obtained gave 5.22 g of the object compound (8.70 mmol), an ivory powder: 87% yield.

NMR (D$_2$O, 300 MHz): δ 1.07 (t, 3H, J=6.9Hz, CH$_2$ CH$_3$), 1.22(s, 3H, C-CH$_3$), 1.96, 2.01, 2.03(9H, 3N-CO CH$_3$), 2.54(s, 3H, N-CH$_3$), 2.60(d, 1H, J=9.5Hz, H-3"), 4.80–4.94(m, 1H, H-4'), 4.98(d, 1H, J=4.0 Hz, H-1"), 5.49 (d, 1H, J=2.0 Hz, H-1').

Analysis calculated for: C$_{27}$H$_{47}$N$_5$O$_{10}$·1.5H$_2$O
Calculated: C, 51.58; H, 8.02; N, 11.14
Found: C, 51.50; H, 8.13; N, 11.70

B. Process B 3.0 g of sodium borohydride (0.80 mol) was slowly added to 15.2 ml of glacial acetic acid (0.26 mol) in 40 ml of chloroform at 18°–20° C. The addition rate was adjusted with observing the generation rate of hydrogen gas. To this, a 3,2',6'-N-triacetylsisomicin (III-a) (5.73 g, 0.01 mol) solution in chloroform (50 ml) was added, and then, stirred at a temperature of 0°–50° C. for 20 hrs. After being cooled to a temperature of 25°±5° C., the resulting solution was neutralized with a saturated sodium hydroxide solution. This neutralized solution was diluted with 50 ml of ethanol, extracted three times with 50 ml of chloroform, and distilled in vacuo. The resultant residue was subjected to column chromatography on silica gel by use of an eluting solution comprising chloroform, methanol and 14% ammonia water in a ratio of 30:10:1. Freeze drying of the eluates thus obtained gave 4.92 g of the object compound (8.200 mmol), an ivory powder: 82% yield.

$^1$H-NMR spectrum showed that this obtained compound is identical to the compound obtained in the Process A in element composition.

EXAMPLE IV

Preparation of 1-N-Ethyl-3,2',6'-tri-N-benzyloxycarbonyl sisomicin (IV-a)

A. Process A

To 4.30 g of 3,2',6'-tri-N-benzyloxycarbonylsisomicin (III-b) (0.005 mol) and 2.40 g of glacial acetic acid (0.04 mol) in 30 ml of chloroform was added 6.35 g of triacetoxy sodium borohydride (0.03 mol), and followed by stirring at 0°–50° C. for 48 hrs. After being cooled to room temperature, the reaction mixture was neutralized with 30 ml of a saturated sodium hydroxide solution, extracted three times with 150 ml of chloroform, and concentrated in vacuo. The resultant residue was subjected to column chromatography on silica gel by use of an eluting solution comprising chloroform, methanol and 7% ammonia water in a ratio of 2:1:1. Freeze drying of the eluates thus obtained gave 3.89 g of the object compound (3.600 mmol), an ivory powder: 72% yield.

mp: 78°–80° C.

NMR (CDCl$_3$, 300MHz): δ 1.07(t, 3H, J=6.9Hz, CH$_2$ CH$_3$), 1.10(s, 3H, C-CH$_3$), 2.57(s, 3H, N-CH$_3$), 4.85(s, 1H, H-4'), 4.49(s, 1H, H-1"), 4.98–5.12(m, 6H, CH$_2$-Ph), 5.35(s, 1H, H-1'), 7.25–7.34(m, 15H, Ph).

Analysis calculated for: C$_{45}$H$_{59}$O$_{13}$·1.5H$_2$O
Calculated: C, 60.32; H, 6.64; N, 7.82
Found: C, 60.50; H, 6.65; N, 7.71

B. Process B

To 10.0 ml of glacial acetic acid (0.14 mol) in 10 ml of chloroform was slowly added 1.5 g of sodium borohydride (0.04 mol) at 0°–20° C. The addition rate was adjusted by observing the generation rate of hydrogen gas. To this, a 3,2',6'-N-benzyloxcarbonylsisomicin (III-b) (4.30 g, 0.005 mol) solution in chloroform (30 ml) was added, and then, stirred at a temperature of 0°–50° C. for 40 hrs. The resulting solution was neutralized with excess 10% sodium hydroxide solution, extracted three times with 150 ml of chloroform, and distilled in vacuo. The resultant residue was subjected to column chromatography on silica gel by use of an eluting solution comprising chloroform, methanol and 7% ammonia water in a ratio of 2:1:1. Freezing dry of the eluates thus obtained gave 3.94 g of the object compound (4.350 mmol), an ivory powder: 87% yield.

$^1$H-NMR spectrum showed that this obtained compound is almost identical to the compound obtained in the Process A in element composition.

Analysis calculated for: C$_{45}$H$_{59}$O$_{13}$·1.5H$_2$O
Calculated: C, 60.32; H, 6.64; N, 7.82
Found: C, 60.48; H, 6.62; N, 7.70

EXAMPLE V

Preparation of 1-N-Ethylsisomicin

A. From 1-N-Ethyl-3,2',6'-tri-N-acetylsisomicin (IV-a)

3.30 g of 1-N-ethyl-3,2',6'-tri-N-acetytsisomicin (0.005 mol) was dissolved in 10 ml of 10% sodium hydroxide at reflux for 41 hours in a nitrogen atmosphere. After being cooled to a temperature of 20°±5° C., the resulting mixture was adjusted o by 1 N sulfuric acid in an ice bath so as to have pH 9, over which 50 ml of isopropanol was then poured. The resulting solution was concentrated by use of a vacuum rotary evaporator and then, added by 40 ml of isopropanol and filtered off the solid matter. The flitrate was distilled in vacuo. The resultant residue was subjected to column chromatography on silica gel by use of an eluting solution comprising chloroform, methanol and 7% ammonia water in a ratio of 40:20:7. Freeze drying of the eluates thus obtained gave 1.90 g of the object compound (4.00 mmol), a brown powder: 80% yield.

mp: 100°–103 ° C.

NMR (D$_2$O, 300 MHz): δ 1.07(t, 3H, J=6.9 Hz, CH$_2$ CH$_3$), 1.21 (s, 3H, C-CH$_3$), 2.53(s, 3H, N-CH$_3$), 3.23(s, 2H, H-6'), 4.90–4.94(m, 1H, H-4'), 5.02(d, 1H, J=4.0 Hz, H-1"), 5.36(d, 1H, J=2.0 Hz, H-1').

B. From 1-N-Ethyl-3, 2',6'-tri-N-tribenzyloxycarbonyl sisomicin (IV-b)

8.0 g of the starting material (0.009 mol) along with 40 ml of dioxane, 200 ml of distilled water and 30 ml of methanol was charged in a hydrogenation reactor and added with acetic acid so as to have pH 3.5–4.0. This solution was stirred for 8 hrs. under hydrogen pressure of 47–50 psi in the presence of 500 mg of 5% Pd/C. The solution obtained after completion of reaction was filtered with celite and then, subjected to ion exchange chromatography using an exchanger such as that sold under the trademark designation "IRA-401S" so as to give pH 9.5. The flitrate was distilled in vacuo. The resultant residue was subjected to column chromatography on silica gel by use of an eluting solution comprising chloroform, methanol and 7% ammonia water in a ratio of 40:20:7. Freeze drying of the eluates thus obtained gave 2.55 g of the object compound (4.00 mmol): 60% yield.

$^1$H-NMR spectrum showed that this obtained compound is almost identical to the compound obtained in the Process A in element composition.

EXAMPLE VI

Preparation of 1-N-Ethylsisomicin sulfate 1.30 g of 1-N-ethylsisomicin (2.70 mmol) obtained in Example V was dissolved in 10 ml of water and adjusted by slow addition of 6.82 ml of a 1 N aqueous sulfuric acid solution (6.80 mmol) so as to have pH 4.5. The resulting solution was added with 250 ml of methanol, filtered off a solid and dried, to give a stoichiometry of the object compound, a white powder.

mp: 182-(dec.)

NMR (D20,300 MHz): δ 1.33(t, 3H, J=7.2Hz, CH$_2$CH$_3$), 1.38(s, 3H, C-CH$_3$), 2.10(q, 2H, J=7.2, 15.5 Hz, NHCH$_2$CH$_3$), 2.96(s, 3H, N-CH$_3$), 3.53(d, 1H, J=13.0 Hz, H-3"), 5.17(m, 1H, H-4'), 5.22(d, 1H, J=2.4 Hz, H-1"), 5.65(s, 1H, H-1').

$^{13}$C-NMR (D$_2$O): δ 10.95(C-1, N-CH$_2$CH$_3$), 20.79(C-1, N-CH$_2$CH$_3$), 23.71(C-4", CH$_3$), 25.30(C-3'), 34.87(c-2), 40.58(C-3", N-CH$_3$), 41.00(C-6'), 46.02 (C-3), 48.17(C-2'), 56.24(C-1), 63.73(C-3"), 66.64(C-5), 67.62(C-2"), 69.94(C-5) 73.52(C-4"), 78.85(C-4), 82.84(C-6), 97.23(C-4'), 100.32(C-1'), 101.49(C-1"), 143.64(C-5').

Analysis calculated for: C$_{21}$H$_{41}$N$_5$O$_7$.2.5H$_2$O

Calculated: C, 34.99; H, 6.43; N, 9.72; S, 11.12; O, 37.74
Found: C, 34.50; H, 6.41; N, 9.87; S, 11.54; O, 37.68

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for preparing 1-N-ethylsisomicin represented by the following structural formula I, comprising the steps of:

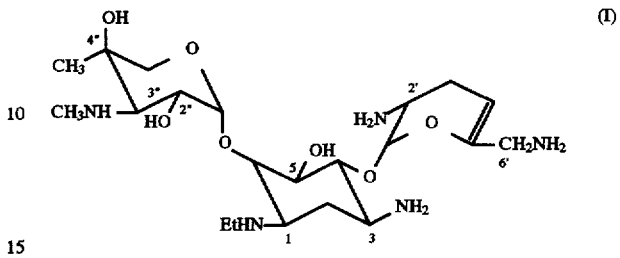

chelating sisomicin with a chelating agent in a protic solvent;

protecting the 3-, 2'- and 6'-amino groups of the chelated sisomicin derivative with an acylating reagent;

removing the chelating agent from the sisomicin derivative by use of ammonia water, to obtain a 3, 2',6-N-trisubstituted sisomicin derivative;

reacting the trisubstituted sisomicin derivative with an ethylating reagent selected from the group consisting of a mixture of acetic acid and monoacetoxy sodium borohydride a mixture of acetic acid and diacetoxy sodium borohydride, a mixture of acetic acid and triacetoxy sodium borohydride, a mixture of acetic acid and monoacetoxy potassium borohydride, a mixture of acetic acid and diacetoxy potassium borohydride, a mixture of acetic acid and triacetoxy potassium borohydride, a mixture of acetic acid and sodium borohydride, and a mixture of acetic acid and potassium borohydride, in an aprotic organic solvent, to selectively ethylate the 1-amino group of the trisubstituted sisomicin derivative; and deprotecting the ethylated sisomicin derivative.

2. A method in accordance with claim 1, wherein said protic solvent is selected from the group consisting of methanol, ethanol, propanol, isopropanol and any mixtures thereof.

3. A method in accordance with claim 1, wherein said acylating reagent is anhydrous acetic acid or N-benzyloxycarbonyloxy succinimide.

4. A method in accordance with claim 1, wherein said aprotic solvent is selected from the group consisting of chloroform, methylene chloride, carbon tetrachloride, tetrahydrofuran, dimethoxyethane, 1,4-dioxane, benzene, toluene, acetonitrile, propionitrile, benzonitrile and any mixtures thereof.

* * * * *